United States Patent [19]
Meiberg et al.

[11] Patent Number: 5,043,275
[45] Date of Patent: Aug. 27, 1991

[54] PROCESS FOR THE FERMENTATIVE OXIDATION OF REDUCING DISACCHARIDES

[75] Inventors: Johannes B. M. Meiberg, Kropswolde; Peter M. Bruinenberg, Hoogezand; Boelem Sloots, Veendam, all of Netherlands

[73] Assignee: Coöperatieve Verkoop- en Productievereniging van Aardappelmeel en Derivaten 'ABEVE' B.A., Netherlands

[21] Appl. No.: 482,924

[22] Filed: Feb. 21, 1990

[30] Foreign Application Priority Data

Feb. 21, 1989 [NL] Netherlands ............ 8900420

[51] Int. Cl.$^5$ .................. C12P 7/58; C12P 19/12; C12R 1/38
[52] U.S. Cl. ...................... 435/137; 435/100; 435/146; 435/253.3; 435/874
[58] Field of Search ........... 435/137, 100, 146, 253.3, 435/874

[56] References Cited

U.S. PATENT DOCUMENTS

| | | | |
|---|---|---|---|
| 3,862,005 | 1/1975 | Miyake et al. | 435/874 |
| 3,899,604 | 8/1975 | Miyake et al. | |
| 4,246,348 | 1/1981 | Lanzilotta et al. | 435/137 |
| 4,345,031 | 8/1982 | Coppens | 435/137 |

FOREIGN PATENT DOCUMENTS 1249347 10/1971 United Kingdom ............ 435/137

OTHER PUBLICATIONS

F. H. Stodola et al., "Oxidation of Lactose and Maltose to Bionic Acids by Pseudomonas", Chemical Abstracts, vol. 42, No. 6, Mar. 20, 1948, Cols. 1983h–1984b.

Y. Sato et al., "Lactulose and Lactobionic Acid from Lastose", Chemical Abstracts, vol. 74, No. 25, Jun. 21, 1971, p. 636, Abstract No. 142 296c.

Primary Examiner—Herbert J. Lilling

[57] ABSTRACT

A process for the fermentative oxidation of reducing disaccharides to aldobionic acids, wherein a fermentation medium containing a reducing disaccharide and growth components is treated under aerobic conditions with cell material obtained by the growth of microorganisms belonging to the species Pseudomonas cepacia.

5 Claims, No Drawings

PROCESS FOR THE FERMENTATIVE OXIDATION OF REDUCING DISACCHARIDES

The present invention relates to the fermentative oxidation of reducing disaccharides, such as maltose and lactose, using the microorganism *Pseudomonas cepacia*. By the oxidation of these disaccharides aldobionic acids, such as maltobionic acid or lactobionic acid, or their salts can be prepared.

U.S. Pat. No. 3,899,604 discloses the use of maltobionic acid as a nutrient acid. Maltobionic acid has a mildly sour flavour and also contributes to the viscosity of food products in which it is contained. Furthermore, maltobionic acid may enhance the natural smell and taste of certain food products (flavour improver) as described in U.S. Pat. No. 3,829,583.

U.S. Pat. No. 3,862,005 discloses a process for the fermentative oxidation of disaccharides to aldbionic acids by means of the microorganism *Pseudomonas graveolens* or *Pseudomonas fragi*. The process is explicitly described for the conversion of maltose into maltobionic acid. This process comprises, among others, the following three steps, namely the growth of the microorganism (growth phase), the separation of the grown cells from the growth medium (separation step), and the oxidation of the disaccharides by means of enzymes present in the cell material (production phase). A disadvantage of this process is the necessity of separating the cell material from the growth medium before starting the production phase in another medium. This is a result of the fact that during the growth phase, too, said microorganisms use the disaccharide (e.g., maltose) as a carbon and energy source.

The present invention relates to the fermentative production of aldobionic acids, such as maltobionic acid or lactobionic acid, by means of the microorganism *Pseudomonas cepacia*. This process consists essentially of 2 phases, namely the growth phase and the production phase. The growth medium comprises different mineral substances necessary for the growth of the microorganism and further a carbon and energy source (e.g., glucose) and a reducing disaccharide (e.g., maltose or lactose). In the growth phase substantially cell material (biomass) is formed by conversion of the glucose, said cell material comprising the enzyme dehydrogenase, which catalyses the formation of aldobionic acid. During the growth phase the disaccharides present are not used as a carbon source. These disaccharides induce the dehydrogenase, resulting in that in the growth phase the formation of aldobionic acid already takes place to a limited extent.

After sufficient cell material has been formed in the fermenter during the growth phase, the production phase can be carried out in the same fermenter without the necessity of first separating the cell material. For this purpose, an additional dose of disaccharide (e.g., maltose or lactose) is added to the fermentation medium. Moreover, an additional amount of carbon source (e.g., glucose and/or yeast extract) is added to the fermentation medium to prevent a strong deterioration of the amount of active cell material in the fermenter during the production phase. During the production phase the disaccharide is converted almost exclusively into the corresponding aldobionic acid or a salt thereof.

Suitable microorganisms capable of being used according to the invention are the strains *Pseudomonas cepacia* CBS 659.88 and *Pseudomonas cepacia* CBS 658.88, both deposited with the Centraalbureau voor Schimmel-cultures of Baarn, the Netherlands, on Oct. 26, 1988 at Dosterstraat 1, Postlus 273,3740 AG-BAARN.

The fermentation conditions may vary within wide limits. The fermentation temperature preferably ranges from 20° to 50° C. The pH of the fermentation medium preferably ranges from 5 to 8. During the fermentation the pH of the fermentation medium is kept approximately neutral, preferably by addition (titration) of aqueous alkaline solutions, e.g., of NaOH or KOH. The fermentation medium is preferably stirred and aerated. The disaccharides to be converted may be added in pure form. However, there can also be used products rich in the relevant disaccharide, such as maltose syrups or starch hydrolysates which contain relatively much maltose. The duration of the fermentation depends on, among others, the amount of biomass formed, the composition of the fermentation medium and the fermentation conditions. The fermentation may be terminated by removal of the cell material from the fermentation medium, e.g., by filtration. The resulting oxidation efficiencies (mole of disaccharide employed calculated on mole of aldobionic acid produced) may amount to approximately 70 to 95%. The invention will be explained with reference to the following examples.

EXAMPLE 1

In a laboratory fermenter (capacity 2 l; makers Applikon) a growth medium was composed which consisted of the following components:

| | |
|---|---|
| Distilled water | 700 ml |
| $(NH_4)_2SO_4$ | 2.8 g |
| $K_2HPO_4$ | 0.98 g |
| $MgSO_4.7H_2O$ | 0.14 g |
| Trace solution | 3.5 ml |

The trace solution contains the following components:

| | |
|---|---|
| $FeCl_2.4H_2O$ | 2 g/l |
| $H_3BO_3$ | 0.05 g/l |
| $ZnCl_2$ | 0.05 g/l |
| $CuCl_2$ | 0.03 g/l |
| $MnCl_2.4H_2O$ | 0.5 g/l |
| $(NH_4)_6Mo_7O_{24}.4H_2O$ | 0.05 g/l |
| $AlCl_3$ | 0.5 g/l |
| $CoCl_2.6H_2O$ | 0.05 g/l |
| $NiCl_2$ | 0.05 g/l |
| EDTA | 0.5 g/l |
| HCl (concentrated) | 1 ml/l |

This growth medium was sterilized for 20 minutes at 120° C. Then separately sterilized aqueous solutions of 8 g glucose and 2 g maltose were added. After cooling to the fermentation temperature of 30° C. the pH of the medium was adjusted to pH 7 with an aqueous KOH solution. The whole was inoculated with 100 ml preculture of *Pseudomonas cepacia* CBS 659.88, cultured in an Erlenmeyer on the same medium as the main culture. During the growth phase, aeration was effected at a rate of 40 l/h. After sufficient cell material was formed in the growth phase, a total of 300 ml of an aqueous maltose/glucose solution (maltose content 350 g/l; glucose content 20 g/l) was added in 3 equal portions. During the production phase the aeration was increased to 60 l/h. During the whole fermentation titration was effected with an aqueous solution of KOH to maintain the pH of the medium at about 7. The fermentation was terminated 48 hours after addition of the maltose/glucose solution. At that moment approximately 95% by weight of the added maltose had been converted into maltobionic acid. The cell material was removed from the reaction mixture by centrifugation. To the supernatent were then added 1 g/l filtration aid (Dicalite) and 4 g/l activated carbon (Norit SX 2). After 1 hour conditioning at 40° C. the reaction mixture was filtered over a paper filter. The clear liquid was thickened by evaporation (Rotavapor) to 70° Brix. Analysis with thin-layer chromatography showed that the worked-up reaction mixture contained only maltobionic acid and maltose.

EXAMPLE 2

In the laboratory fermenter of Example 1, 100 g maltose were dissolved in 700 ml distilled water. After the pH of the solution was adjusted to 3, the whole was sterilized for 20 minutes at 110° C. Then 500 ml of a sterilized aqueous solution were added which contained the following growth components:

| | |
|---|---|
| $(NH_4)_2SO_4$ | 4.2 g |
| $K_2HPO_4$ | 0.98 g |
| $KH_2PO_4$ | 0.56 g |
| $MgSO_4.7H_2O$ | 0.14 g |
| Trace solution | 3.5 ml |
| Yeast extract | 1.5 g |
| Glucose | 10.8 g |

Then the medium was cooled to 30° C. and the pH was adjusted to 7 with an aqueous NaOH solution. Subsequently, the fermentation was started by adding 100 ml inoculation material of *Pseudomonas cepacia* CBS 658.88 originating from an Erlenmeyer-preculture. After 24 and 48 hours, respectively 200 ml and 100 ml of an aqueous maltose/glucose solution (maltose content 600 g/l; glucose content 30 g/l) were added. During the fermentation, titration was effected with NaOH solution to maintain the pH at about 7. After 72 hours the fermentation was terminated. The product was worked up further as described in Example 1. The resulting concentrated solution contained 72% maltobionic acid (on dry matter).

EXAMPLE 3

In the laboratory fermenter of Example 1 the microorganism *Pseudomonas cepacia* CBS 659.88 was cultured. The medium for the growth phase had the following composition:

| | |
|---|---|
| $(NH_4)_2SO_4$ | 8.4 g/l |
| $K_2HPO_4$ | 2 g/l |
| $MgSO_4.7H_2O$ | 0.28 g/l |
| Yeast extract | 3 g/l |
| Trace solution | 7 ml/l |

To 500 ml of this sterilized medium were added 150 ml sterilized glucose solution to obtain a glucose concentration of 21.6 g/l. Then the fermentation temperature was adjusted to 30° C. The pH of the medium was adjusted to 7 with NaOH solution. The fermentation was started by adding 100 ml inoculation material from an Erlenmeyer with a preculture of *Pseudomonas cepacia* CBS 659.88. After the microorganism had grown sufficiently, 750 ml of an aqueous lactose/glucose solution (lactose content 560 g/l; glucose content 10 g/l) were added. During the fermentation, filtration was effected with NaOH solution to maintain the pH of the medium at about 7. The fermentation was terminated after 50 hours. The product was worked up as described in Example 1. The content of lactobionic acid (in the form of the Na salt) in the final product was 85% by weight (on dry matter).

We claim:

1. A process for the fermentative oxidation of reducing disaccharides to aldobionic acids, comprising treating under aerobic conditions a fermentation medium containing a reducing disaccharide and growth components with a cell material obtained by growing microorganisms belonging to the species *Pseudomonas cepacia* in a growth medium, without separating the cell material from the growth medium in which it has been produced.

2. A process according to claim 1, characterized in that the cell material is obtained by the growth of the strain *Pseudomonas cepacia* CBS 659.88.

3. A process according to claim 1, characterized in that the cell material is obtained by the growth of the strain *Pseudomonas cepacia* CBS 658.88.

4. A process according to claims 1, 2 or 3, characterized in that maltobionic acids or salts thereof are prepared by the fermentative oxidation of maltose-containing substrates.

5. A process according to claims 1, 2 or 3, characterized in that lactobionic acid or salts thereof are prepared by the fermentative oxidation of lactose-containing substrates.

* * * * *